United States Patent
Chang et al.

(10) Patent No.: US 8,215,775 B2
(45) Date of Patent: Jul. 10, 2012

(54) METHOD FOR ANALYZING TEAR FILM THERMOGRAPH OF CONTACTLESS TEAR FILM THERMAL IMAGER

(75) Inventors: O Chang, Taipei (TW); Chung-Hwa Chang, Taipei (TW); Po-Hsuan Liu, Taipei (TW); Ming-Hong Wu, Taipei (TW)

(73) Assignee: United Integrated Services Co., Ltd. (TW)

( * ) Notice: Subject to any disclaimer, the term of this patent is extended or adjusted under 35 U.S.C. 154(b) by 135 days.

(21) Appl. No.: 12/876,948

(22) Filed: Sep. 7, 2010

(65) Prior Publication Data

US 2012/0057126 A1  Mar. 8, 2012

(51) Int. Cl.
*A61B 3/14* (2006.01)
*A61B 3/10* (2006.01)
*A61B 3/00* (2006.01)

(52) U.S. Cl. .................... 351/206; 351/246; 351/221

(58) Field of Classification Search ........... 351/200–246
See application file for complete search history.

(56) References Cited

U.S. PATENT DOCUMENTS

| | | | |
|---|---|---|---|
| 7,922,328 B2 * | 4/2011 | Dai et al. | 351/205 |
| 7,988,294 B2 * | 8/2011 | Korb et al. | 351/221 |

\* cited by examiner

*Primary Examiner* — Mohammed Hasan
(74) *Attorney, Agent, or Firm* — Hershkovitz & Associates, LLC

(57) ABSTRACT

A method for analyzing tear film thermograph of contactless tear film thermal imager has steps of sequentially loading multiple thermographs of a tear film, recording a maximum and a minimum of temperatures for a region of interest of each one of the thermographs, dividing the thermograph into at least one temperature zone in accordance with the maximum and minimum temperatures recorded in the last step, and recording a size, a location and a bordering temperature of each one of the at least one temperature zone, analyzing a pattern and temperature variation of each one of the at least one temperature zone, and classifying stability of the tear film. The patterns of the temperature zones can be identified through circularity computation, mosaic and temperature gradient analysis. Accordingly, tear film break up patterns can be classified with the method to facilitate doctors to diagnose a dry eye patient.

9 Claims, 12 Drawing Sheets

METHOD FOR ANALYZING TEAR FILM THERMOGRAPH OF CONTACTLESS TEAR FILM THERMAL IMAGER

BACKGROUND OF THE INVENTION

1. Field of the Invention

The present invention is related to a method for analyzing tear film thermograph of contactless tear film thermal imager, and more particularly to a method for analyzing team film thermograph using pattern analysis and parametric analysis technique.

2. Description of the Related Art

Human eyes have a tear film formed on a surface of the cornea to constitute a protection film. The tear film from inside out has a mucus layer, an aqueous layer and a lipid layer to combine into a tear in human eyes. The mucus layer, the aqueous layer and the lipid layer are functionally complementary. The lipid layer serves to prevent water from vaporizing, and the mucus layer facilitates to uniformly spreads tear over and closely contacts with the surface of the cornea.

When a healthy eye blinks, the tear film on the surface of the cornea is refreshed by a new tear drained through a canaliculus and the nasal cavity. However, an eye with the dry eye syndrome has worse secretion and refresh function than a normal eye. Usually, the dry eye syndrome can be confirmed by certain intrusive tests, such as Schirmer test or TBUT test (Tear-film Break Up Time). After giving an eye anesthetic drops thrice, the former test places a slender filter paper strip beneath the lower eyelid and observes a wet length of the filter paper strip after few minutes. The latter test gives drops of fluorescent dye in an eye with the dry eye syndrome and uses slit lamp to observe the first tear break up time after the eye is opened. As the foregoing tests intrude eyes with either filter paper or fluorescent dye, the process of the testing is uncomfortable to patients with the dry eye syndrome. On the other hand, disadvantages of low repeatability and high variability also exist in the foregoing tests.

To solve the aforementioned issues, an infrared thermal imager is employed to take thermographs of the front surface of an eyeball for a patient with dry eye syndrome, keep track of precise temperature variation of a specific location of the cornea within a unit time, acquire a K value and a temperature drop difference $\Delta T$ of a temperature-dropping curve in accordance with the temperature variation in a time sequence, and provide a judgment to doctors to diagnose the patient based on a curve with the optimized K and $\Delta T$. Such device acquires images of eyeball for the patient in a contactless manner and verifies the syndrome after an analysis, thereby effectively eliminating the anxiety and fear of patient during the test process and simultaneously enhancing the accuracy of the test.

Clinically, the tear-film break up pattern and lasting time duration vary with patients contracting dry eye syndrome. Each tear-film break up pattern represents a different symptom and different severity. However, the analysis of the tear film break up pattern must fully rely on doctors' judgment and the tear film break up patterns basically associate with recognition of similar images. Due to irregular break up forms of tear films, different doctors may end up with different recognition results and diagnosing judgments, thus impacting on accumulation of clinical case studies and diagnosing experience.

SUMMARY OF THE INVENTION

An objective of the present invention is to provide a method for analyzing tear film thermograph of contactless tear film thermal imager using pattern analysis and parametric analysis technique.

To achieve the foregoing objective, the method for analyzing tear film thermograph of contactless tear film thermal imager has steps of:

sequentially loading multiple thermographs of a tear film;

recording a maximum and a minimum of temperatures for a region of interest of each one of the thermographs;

dividing the thermograph into at least one temperature zone in accordance with the maximum and minimum temperatures recorded in the last step, and recording a size, a location and a bordering temperature of each one of the at least one temperature zone;

analyzing a pattern and temperature variation of each one of the at least one temperature zone; and classifying stability of the tear film.

In the step of analyzing a pattern and temperature variation, the pattern of each one of the at least one temperature zone is analyzed by circularity computation, mosaic processing and temperature gradient analysis to classify the tear film as the following types:

type A having a temperature distribution taking a form of concentric circles and constantly dropping temperature;

type B having a temperature distribution taking a form of blurred concentric circles with a uniformly distributed gray level;

type C having a temperature distribution taking a form of dark stripes of tree branches, cracks or parallel lines that are not moving upwardly;

type D having a temperature distribution taking a form of a horizontal dark stripe that appears at or above a center of the cornea and moves upwardly over time;

type E having a temperature distribution taking a form of concentric circles and rapidly dropping temperature in first few seconds then stopping dropping temperature when a minimum temperature is reached;

type F having a temperature distribution taking a form of dark stripes and horizontally expanding or moving upwardly over time; and Others not pertaining to any one of type A to type F.

The mentioned type A to type F patterns stand for the tear films having stability differing in degree. Thermographs of a dry eye patient can be analyzed by the aforementioned pattern analysis and parametric analysis and then adequately classified, thereby facilitating doctors to correctly diagnose an eye with the dry eye syndrome.

Other objectives, advantages and novel features of the invention will become more apparent from the following detailed description when taken in conjunction with the accompanying drawings.

DETAILED DESCRIPTION OF THE INVENTION

Figure 1:
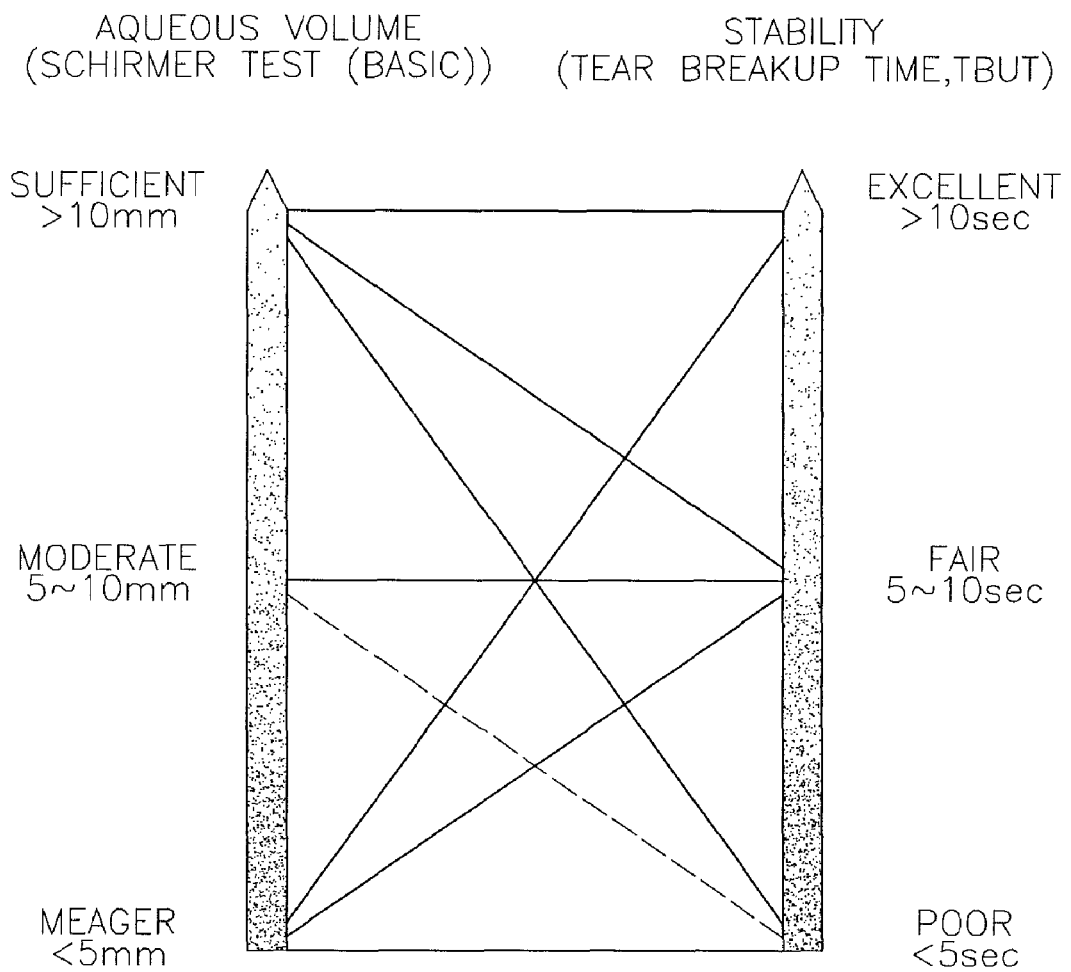
FIG. 1 is a chart illustrating aqueous volumes acquired in the Schirmer Test versus stability acquired in the TBUT test.

As the present invention is used to categorize patterns of various tear films, tear film patterns observed clinically are classified and described as follows:

With reference to FIG. 1, two parallel vertical arrows respectively represent an aqueous volume of a tear film and a stability of a tear film. On the left side, the lower an aqueous volume goes down along the aqueous volume scale, the more deficient the aqueous volume is. On the other hand, the higher an aqueous volume goes up along the aqueous volume scale, the more sufficient the aqueous volume is. On the right side, the lower a stability goes down along the time scale, the worse the stability is. The higher a stability goes up along the time scale, the better the stability is. When different aqueous volumes crossly correlate to different stability, various tear film patterns appear to correspond to the correlated aqueous volumes and the stability. The types of tear film patterns and the corresponding characteristics are further summarized as follows, in which thermographs of the tear film on an eyeball of a testee is taken by a far infrared thermal imager after the testee closes and then opens the eye, and the far infrared thermal imager possesses a temperature analysis function.

Figure 2A:
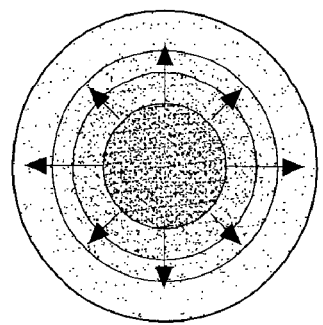
FIGS. 2A to 2F are schematic views showing tear film patterns recognized by a method for analyzing tear film thermograph of contactless tear film thermal imager in accordance with the present invention.
Figure 3A:
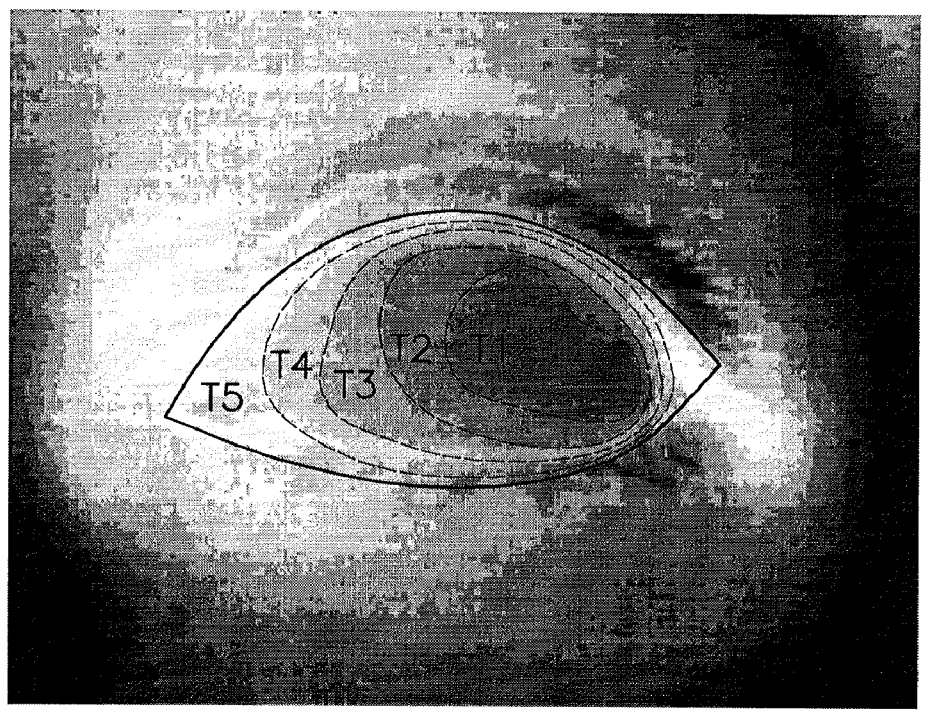
FIGS. 3A to 3F are thermographs respectively corresponding to the tear film patterns in FIGS. 2A to 2F.

A. With reference to FIGS. 2A and 3A, a temperature distribution of a thermograph taken after the eye is opened is classified as a pattern of concentric circles. After the eye is opened for 4 to 5 seconds, the temperature at a center of the cornea is still dropping. Finally, temperature distribution levels whose number is at least four temperature levels specified by different gray levels are noticeable on the thermograph, and the temperature distribution levels are still clearly visible 6 seconds after the eye is opened. In FIG. 3A, the temperature distribution levels are represented by T1 to T5.

Figure 2B:
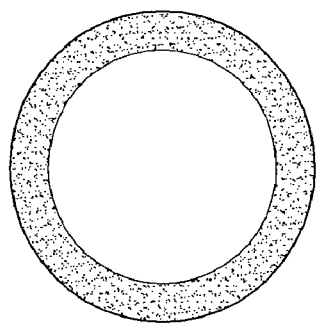
Figure 3B:
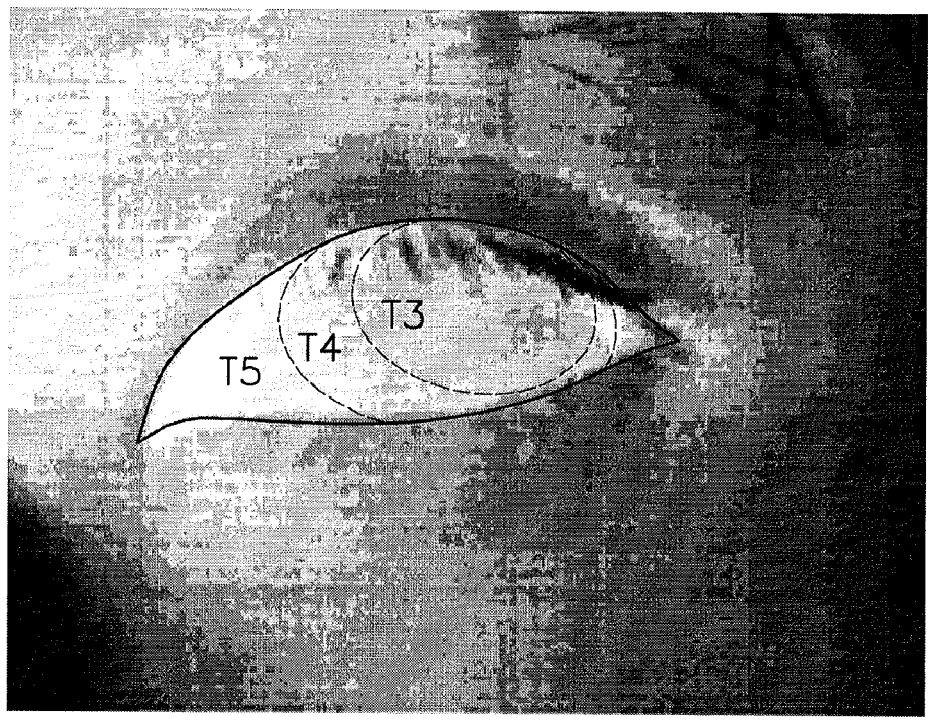

B. With reference to FIGS. 2B and 3B, a temperature distribution of a thermograph taken after the eye is opened is classified as a pattern of blurred concentric circles represented by few temperature distribution levels which is less than four temperature levels. In FIG. 3B, the temperature distribution levels are represented by T3 to T5. Compared with the most inner circle temperature distribution T1 of type A, the most inner circle temperature distribution T3 of type B is much brighter than the most inner circle temperature distribution T1 of type A. The blurred concentric circles are visually bright with a uniformly distributed gray level and vary little even after 6 seconds the eye is opened.

Figure 2C:
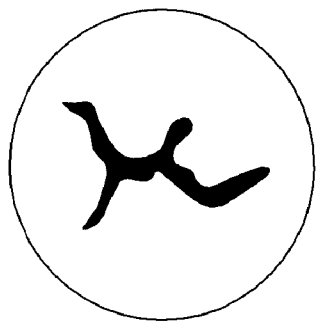
Figure 2C:
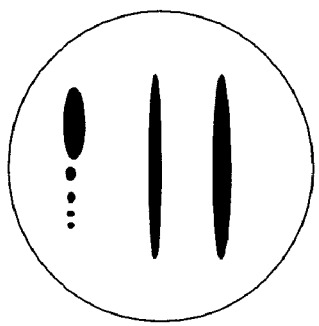
Figure 2C:
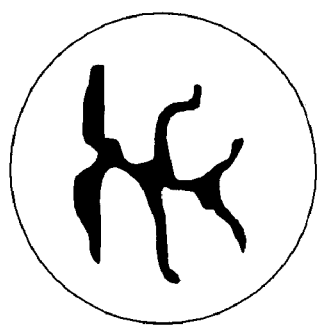
Figure 3C:
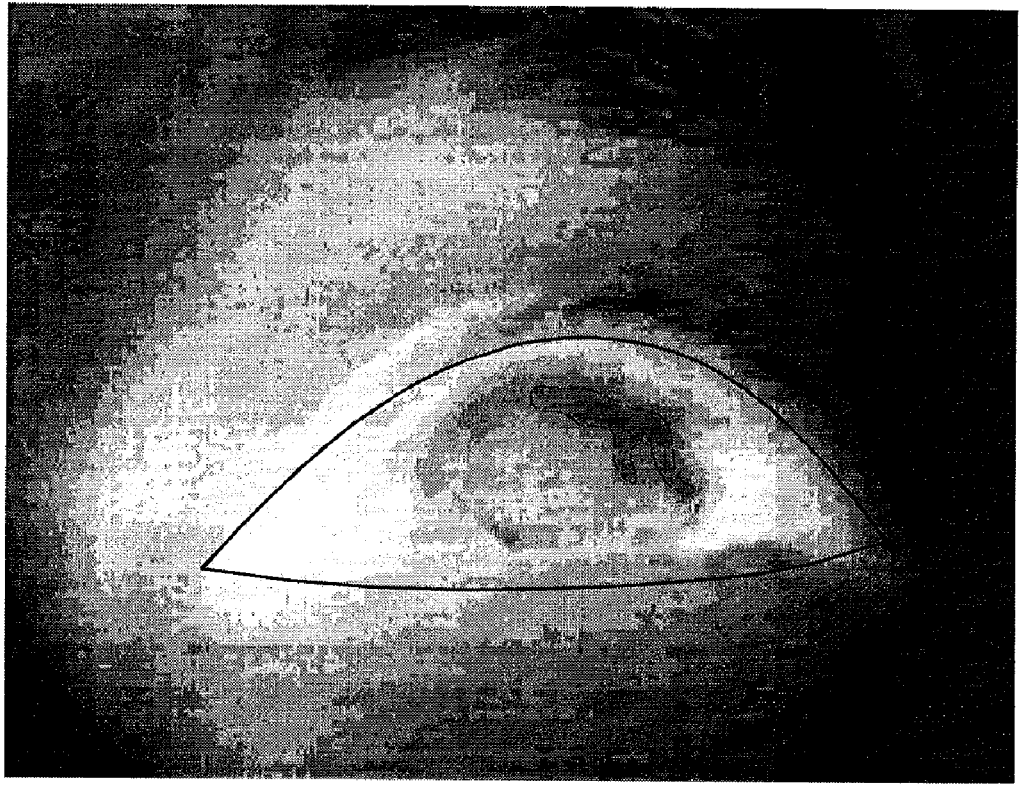

C. With reference to FIGS. 2C and 3C, after the eye is opened, a temperature distribution of a thermograph taken is classified as a pattern of dark stripes taking a form of tree branches, cracks or straight lines. The temperatures keep dropping. However, the dark stripes do not move upwardly.

Figure 2D:
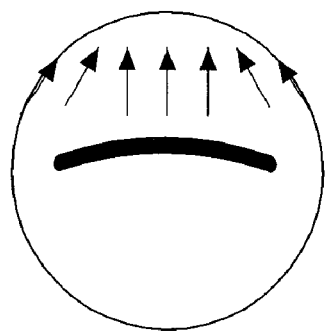
Figure 3D:
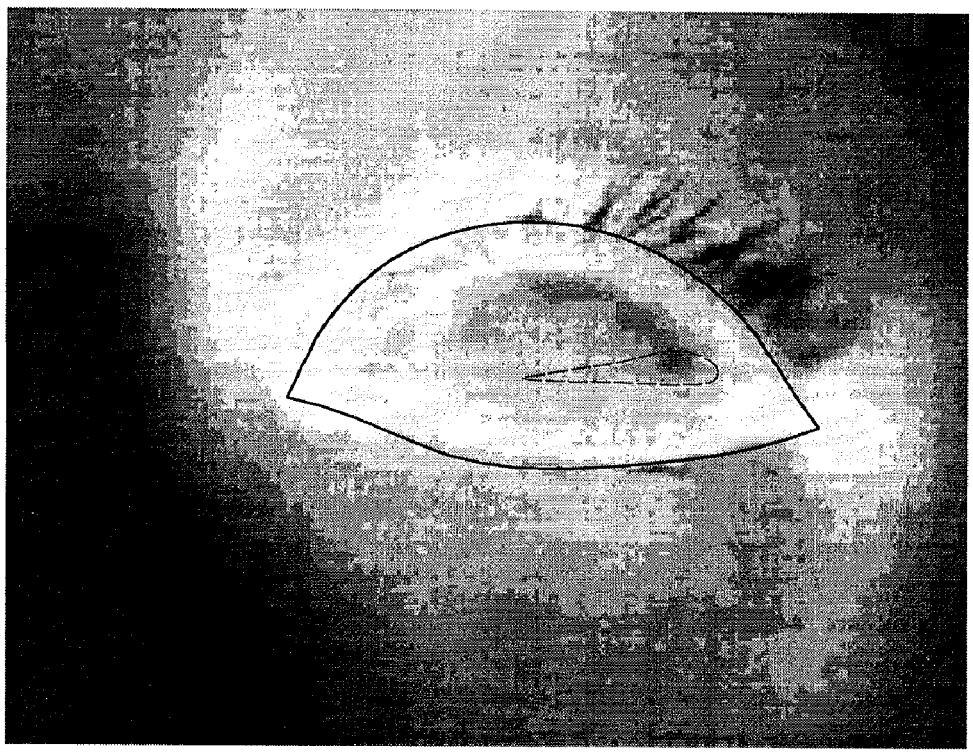

D. With reference to FIGS. 2D and 3D, after the eye is opened, a temperature distribution of a thermograph taken is classified by a pattern of a horizontal dark stripe appearing at or above the center of the cornea. The temperatures do not drop substantially. The horizontal dark stripe moves upwardly over time.

Figure 2E:
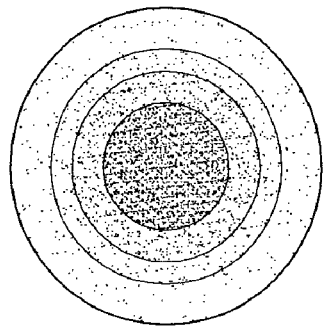
Figure 3E:
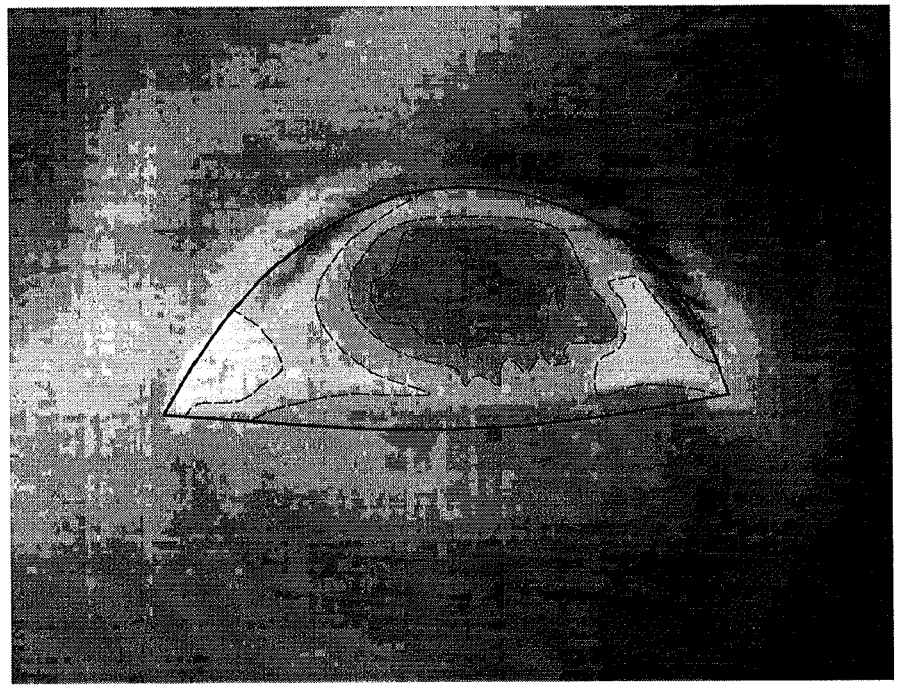

E. With reference to FIGS. 2E and 3E, after the eye is opened, a temperature distribution of a thermograph taken is classified as a pattern of concentric circles. The temperatures drop rapidly to a minimum thereof within 3 to 4 seconds after the eye is opened and stay still then almost without further going down. The temperature levels varies little after the eye is opened for 4 to 6 seconds.

Figure 2F:
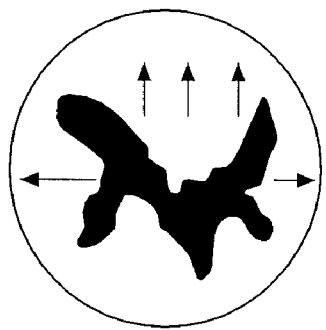
Figure 3F:

F. With reference to FIGS. 2F and 3F, after eye is opened, a temperature distribution of a thermograph taken is classified by a pattern of dark stripes. The temperatures keep dropping after the eye is opened and the temperature drop is lessened when 4 to 5 seconds after the eye is opened. The dark stripes on the cornea gradually expand horizontally and moves upwardly.

The tear film patterns not matching the A-F patterns pertain to others.

The stability of A and B patterns is the best, and the tear films thereof break up 10 seconds after the eye is opened. The stability of E and F patterns is the worst, and the tear films thereof break up within 5 seconds after the eye is opened. The stability of C and D patterns ranks moderately, and the tear films thereof break up 5 to 10 seconds after the eye is opened.

Figure 4:
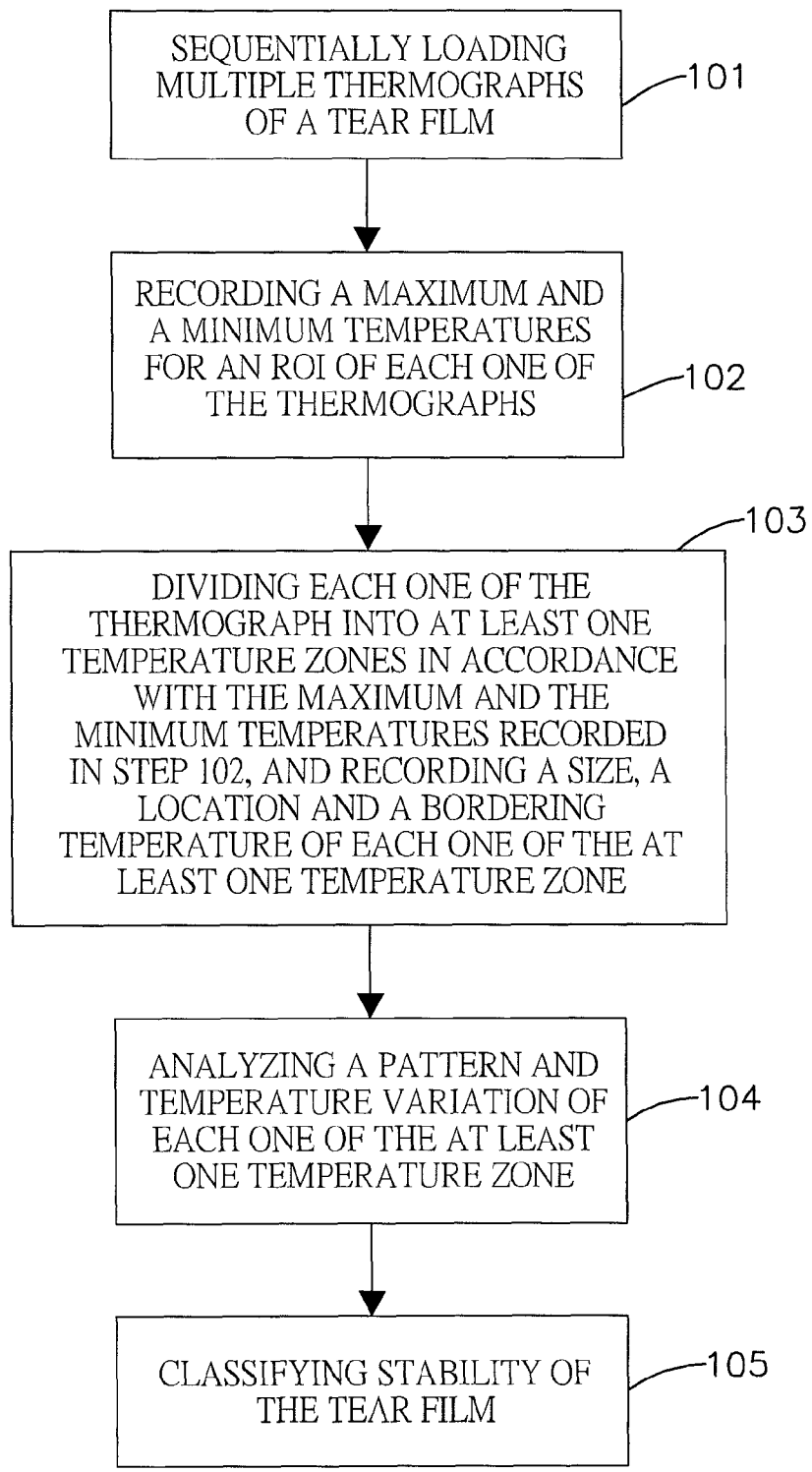
FIG. 4 is a flow diagram of a method for analyzing tear film thermographs in FIGS. 3A to 3F.

As far as the stability of tear film is concerned, the foregoing patterns are the types available clinically. The present invention categorizes the thermographs of tear films obtained by the technique of pattern analysis and parametric analysis to assist doctors in promptly understanding the tear film variation of patients. With reference to FIG. 4, a method for analyzing tear film thermograph of contactless tear film thermal imager in accordance with the present invention has the following steps of:

sequentially loading multiple thermographs of a tear film 101;

recording a maximum and a minimum temperatures for a region of interest (ROI) of each one of the thermographs 102;

dividing each one of the thermograph into at least one temperature zones in accordance with the maximum and the minimum temperatures recorded in Step 102, and recording a size, a location and a bordering temperature of each one of the at least one temperature zone 103;

analyzing a pattern and temperature variation of each one of the at least one temperature zone 104; and classifying stability of the tear film 105.

The thermographs loaded in Step 101 are taken from an identical tear film within a period of time and are used to observe how the tear film varies within 6 seconds. The thermographs are taken at a speed of one thermograph per second within 1 to 6 seconds after the eye is opened. Hence, six thermographs are loaded to respectively indicate states of the tear film at the first, second, third, fourth, fifth and sixth second.

Step 102 targets at a region of interest (ROI) on each one of the thermographs to respectively record the maximum and minimum of the temperature of each one of the ROIs. The ROIs are specifically defined within a range of the cornea. As the far infrared thermal imager alone can determine temperatures of a thermograph and reflect the magnitude of temperature by different colors or gray levels, the ROIs can be identified on the corresponding thermographs and the maximum and minimum of the temperature in each one of the ROIs can be recorded.

Step 103 divides each one of the thermograph into at least one temperature zones after acquiring the maximum and minimum of the temperature in each one of the ROIs. Given the example of the type A tear film, multiple annular temperature zones taking a form of concentric circles appear on the cornea. The size, location and bordering temperature of the annular temperature zones are sequentially recorded.

Step 104 is used to analyze the pattern and temperature variation of each one of the at least one temperature zone. Tools for analyzing the pattern of each one of the at least one temperature zone have circularity computation, mosaic processing, temperature gradient analysis and the like. The equation of circularity computation is expressed as follows:

$$F_{circ} = 4\pi A/P^2$$

where $F_{circ}$ is a circularity factor, A is an area of a temperature zone, and P is a perimeter of the temperature zone.

All thermographs of tear film must go through the circularity computation. Given the example of type A tear film pattern, whether the temperature zones take a form of concentric circles or not can be ascertained through the circularity computation. A singular point of the observed temperature variation is a minimum point having a circularity factor value less than 0.3 or a point having a largest dropping magnitude in its circularity factor value.

Figure 5:
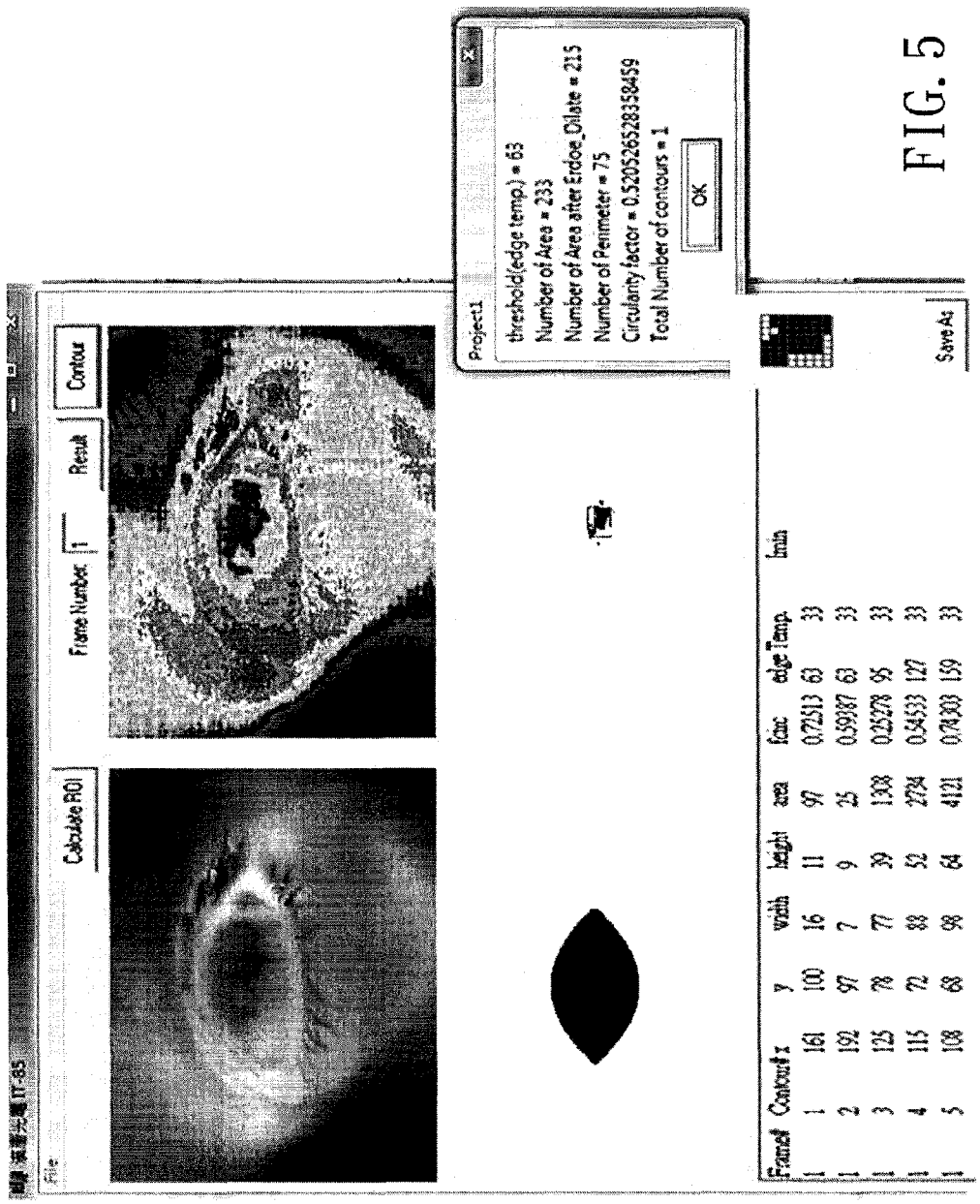
FIG. 5 is an operation interface of a mosaic processing analyzed by the method in FIG. 4.

The mosaic processing is used to represent multiple points in the thermograph with a single value (an average of the multiple points and compared with a binary threshold), thereby simplifying image data to facilitate fast comparison and determination. With reference to FIG. 5, a top right portion remains as a potion of the original thermograph, and the bottom right portion pertains to a result performed with the mosaic processing. The tree branches, cracks, horizontal dark stripes or vertical dark stripes appearing on the thermographs of types C, D and F tear film patterns can be identified after the mosaic processing.

Figure 6:
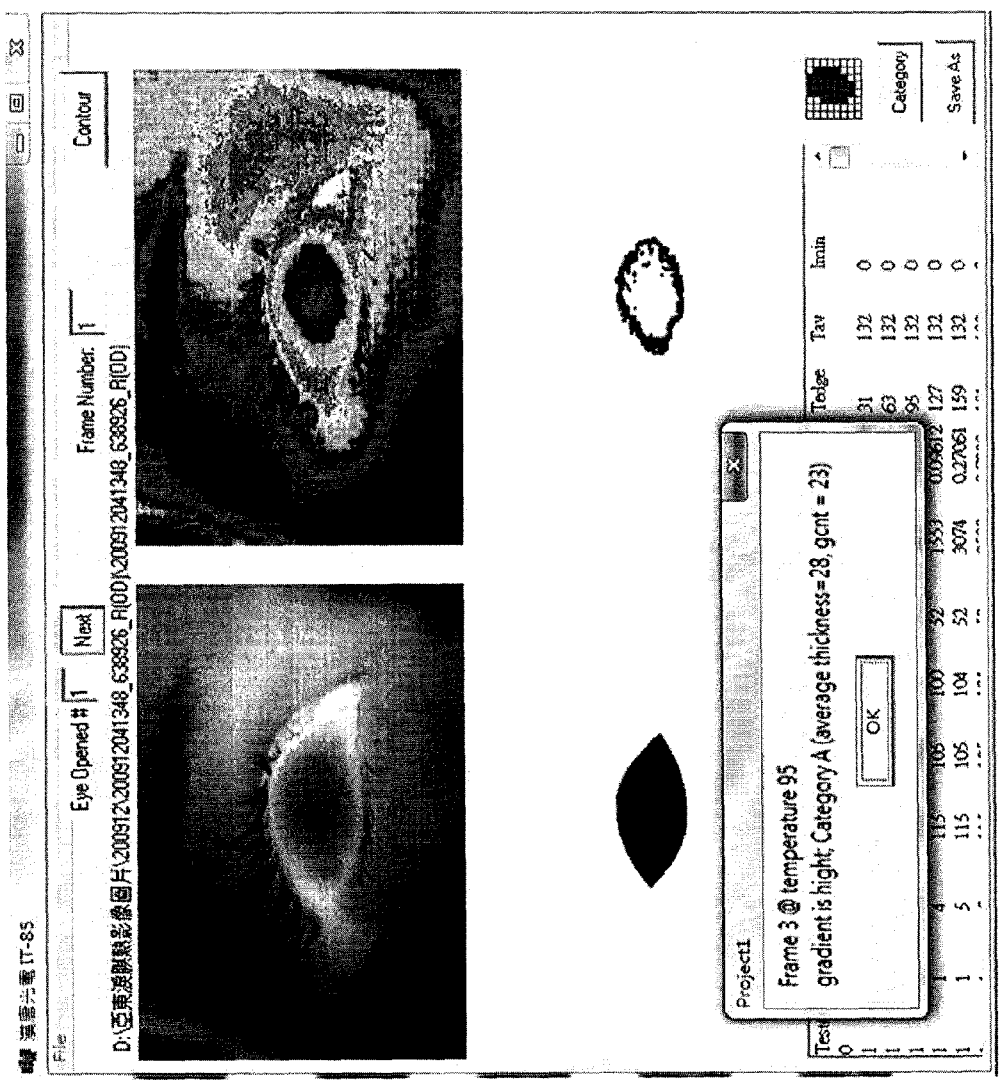
FIG. 6 is an operation interface of a temperature gradient analysis analyzed by the method in FIG. 4.

Moreover, the temperature gradient is a physical quantity used to describe in which direction in a specific environment the temperature varies most rapidly and with what rate the temperature varies. The unit of the temperature gradient is in degrees/unit length (within a specific temperature range). The temperature gradient serves to analyze the pattern and location of each temperature zone as shown in FIG. 6. As for whether the tree branches, cracks or horizontal and vertical dark stripes of the type C, D and F tear film patterns move on the cornea or to which direction they head for to move, both can be determined by the temperature gradient technique.

Besides the foregoing tools, as each one of the temperature zones of each thermograph is recorded with size, location and temperatures thereof, a temperature variability (or called temperature drop range $\Delta T/\Delta t$) can be observed in accordance with the temperatures recorded in each thermograph.

Given the foregoing tools to analyze the pattern of the thermograph, the thermograph of the tear film can be classified (by Step 105 of the method for analyzing tear film thermograph). The classified pattern of the thermograph facilitates doctors to more conveniently diagnose the dry eye syndrome and accumulate more clinical case studies and more diagnosing experience.

Even though numerous characteristics and advantages of the present invention have been set forth in the foregoing description, together with details of the structure and function of the invention, the disclosure is illustrative only. Changes may be made in detail, especially in matters of shape, size, and arrangement of parts within the principles of the invention to the full extent indicated by the broad general meaning of the terms in which the appended claims are expressed.

What is claimed is:

1. A method for analyzing tear film thermograph of contactless tear film thermal imager, comprising steps of:
    sequentially loading multiple thermographs of a tear film;
    recording a maximum and a minimum of temperatures for a region of interest of each one of the thermographs;
    dividing the thermograph into at least one temperature zone in accordance with the maximum and minimum temperatures recorded in the last step, and recording a size, a location and a bordering temperature of each one of the at least one temperature zone;
    analyzing a pattern and temperature variation of each one of the at least one temperature zone; and
    classifying stability of the tear film.

2. The method as claimed in claim 1, wherein the step of analyzing the pattern of each one of the at least one temperature zone comprise acts of:
    a circularity computation computing a circularity factor each one of the at least one temperature zone and determining if the at least one temperature zone are concentric circles;
    a mosaic processing representing multiple points in each one of the thermographs as one point by using an average temperature or a binary threshold of the points to identify tree branches, cracks, horizontal lines and vertical lines on each one of the thermographs; and
    a temperature gradient analysis analyzing to which direction a dark stripe on each one of the thermograph moves.

3. The method as claimed in claim 2, wherein a singular point of the observed temperature variation is a minimum point having the circularity factor less than 0.3 or a point having a largest dropping magnitude in the circularity factor of the point.

4. The method as claimed in claim 1, wherein the pattern of the tear film comprises:
    type A classified as having a temperature distribution taking a form of concentric circles and constantly dropping temperature;
    type B classified as having a temperature distribution taking a form of blurred concentric circles with a uniformly distributed gray level;
    type C classified as having a temperature distribution taking a form of dark stripes of tree branches, cracks or parallel lines that are not moving upwardly;
    type D classified as having a temperature distribution taking a form of a horizontal dark stripe that appears at or above a center of the cornea and moves upwardly over time;
    type E classified as having a temperature distribution taking a form of concentric circles and rapidly dropping temperature then stopping dropping temperature when a minimum temperature is reached; and
    type F classified by a temperature distribution taking a form of dark stripes and horizontally expanding or moving upwardly over time.

5. The method as claimed in claim 2, wherein the pattern of the tear film comprises:
    type A classified as having a temperature distribution taking a form of concentric circles and constantly dropping temperature;
    type B classified as having a temperature distribution taking a form of blurred concentric circles with a uniformly distributed gray level;
    type C classified as having a temperature distribution taking a form of dark stripes of tree branches, cracks or parallel lines that are not moving upwardly;
    type D classified as having a temperature distribution taking a form of a horizontal dark stripe that appears at or above a center of the cornea and moves upwardly over time;
    type E classified as having a temperature distribution taking a form of concentric circles and rapidly dropping temperature then stopping dropping temperature when a minimum temperature is reached; and
    type F classified by a temperature distribution taking a form of dark stripes and horizontally expanding or moving upwardly over time.

6. The method as claimed in claim 3, wherein the pattern of the tear film comprises:
    type A classified as having a temperature distribution taking a form of concentric circles and constantly dropping temperature;

type B classified as having a temperature distribution taking a form of blurred concentric circles with a uniformly distributed gray level;

type C classified as having a temperature distribution taking a form of dark stripes of tree branches, cracks or parallel lines that are not moving upwardly;

type D classified as having a temperature distribution taking a form of a horizontal dark stripe that appears at or above a center of the cornea and moves upwardly over time;

type E classified as having a temperature distribution taking a form of concentric circles and rapidly dropping temperature then stopping dropping temperature when a minimum temperature is reached; and type F classified by a temperature distribution taking a form of dark stripes and horizontally expanding or moving upwardly over time.

7. The method as claimed in claim 4, wherein the pattern of the tear film not pertaining to any one of the type A to type F is classified as other type.

8. The method as claimed in claim 5, wherein the pattern of the tear film not pertaining to any one of the type A to type F is classified as other type.

9. The method as claimed in claim 6, wherein the pattern of the tear film not pertaining to any one of the type A to type F is classified as other type.

* * * * *